United States Patent
Vuong et al.

(10) Patent No.: US 8,170,833 B2
(45) Date of Patent: May 1, 2012

(54) TRANSFORMING METROLOGY DATA FROM A SEMICONDUCTOR TREATMENT SYSTEM USING MULTIVARIATE ANALYSIS

(75) Inventors: Vi Vuong, Fremont, CA (US); Junwei Bao, Palo Alto, CA (US); Yan Chen, Santa Clara, CA (US); Weichert Heiko, Utzberg (DE); Sebastien Egret, Lumbin (FR)

(73) Assignee: Tokyo Electron Limited (JP)

( * ) Notice: Subject to any disclaimer, the term of this patent is extended or adjusted under 35 U.S.C. 154(b) by 53 days.

(21) Appl. No.: 12/336,435

(22) Filed: Dec. 16, 2008

(65) Prior Publication Data

US 2009/0094001 A1    Apr. 9, 2009

Related U.S. Application Data

(63) Continuation of application No. 11/349,773, filed on Feb. 7, 2006, now Pat. No. 7,467,064.

(51) Int. Cl.
*G06F 17/18* (2006.01)
(52) U.S. Cl. ..................................... 702/181
(58) Field of Classification Search .................. 702/181
See application file for complete search history.

(56) References Cited

U.S. PATENT DOCUMENTS

| | | | |
|---|---|---|---|
| 5,351,200 A | 9/1994 | Impink | |
| 5,976,466 A | 11/1999 | Ratner et al. | |
| 6,943,900 B2 | 9/2005 | Niu et al. | |
| 6,952,657 B2 * | 10/2005 | Jahns et al. | 702/182 |
| 6,975,944 B1 * | 12/2005 | Zenhausern | 702/22 |
| 7,092,110 B2 | 8/2006 | Balasubramanian et al. | |
| 7,328,126 B2 | 2/2008 | Chamness | |
| 7,467,064 B2 | 12/2008 | Vuong et al. | |
| 2005/0060103 A1 * | 3/2005 | Chamness | 702/30 |
| 2005/0143952 A1 | 6/2005 | Tomoyasu et al. | |

OTHER PUBLICATIONS

International Search Report and Written Opinion issued on Mar. 27, 2009, in application PCT/US2007/002665 (PCT application claiming priority to U.S. Appl. No. 11/349,773, which is the parent application this application).

Office Action issued on Oct. 25, 2011, in counterpart Chinese Patent Application 200780004926.6. No prior art has been cited in this Office Action.

* cited by examiner

*Primary Examiner* — Aditya Bhat (57) ABSTRACT

Metrology data from a semiconductor treatment system is transformed using multivariate analysis. In particular, a set of metrology data measured or simulated for one or more substrates treated using the treatment system is obtained. One or more essential variables for the obtained set of metrology data is determined using multivariate analysis. A first metrology data measured or simulated for one or more substrates treated using the treatment system is obtained. The first obtained metrology data is not one of the metrology data in the set of metrology data earlier obtained. The first metrology data is transformed into a second metrology data using the one or more of the determined essential variables.

11 Claims, 11 Drawing Sheets

Focus, microns

FIG. 8A

Score for EV3

Focus, microns

TRANSFORMING METROLOGY DATA FROM A SEMICONDUCTOR TREATMENT SYSTEM USING MULTIVARIATE ANALYSIS

This application is a Continuation application of U.S. patent application Ser. No. 11/349,773, entitled TRANSFORMING METROLOGY DATA FROM A SEMICONDUCTOR TREATMENT SYSTEM USING MULTIVARIATE ANALYSIS, filed on Feb. 7, 2006, issued as U.S. Pat. No. 7,467,064, all of which is incorporated herein by reference in its entirety for all purposes.

BACKGROUND

1. Field

The present application relates to transforming metrology data from a semiconductor treatment system, and, more particularly, to transforming metrology data using multivariate analysis.

2. Related Art

In semiconductor manufacturing, metrology is increasingly utilized to ensure that individual process steps, as well as a sequence of process steps, adhere to design specifications. For example, metrology may be employed to identify instances of process drift, and provide data sufficient to establish control schemes for correcting such drift.

While critical dimension scanning electron microscopy (CD-SEM) metrology has been used in the past, the complexity of devices formed on semiconductor substrates and their ever-decreasing feature size (e.g., sub 100 nm technology nodes), coupled with increasingly sophisticated unit process and process integration schemes, have warranted the implementation of optical metrology. In addition to being non-destructive, in-line optical metrology, such as optical scatterometry, can be used for robust Advanced Process Control (APC).

In optical scatterometry, one application includes the use of periodic structures that are formed on semiconductor substrates in close proximity to the locations for the formation of operating structures in semiconductor devices. By determining the profile of the periodic structures, the quality of the fabrication process utilized to form the periodic structures, and by extension the operating structure of the semiconductor device proximate the periodic structures, can be evaluated.

In general, optical scatterometry involves illuminating the periodic grating with electromagnetic (EM) radiation, and measuring the resulting diffracted signal. The characteristics of the measured diffraction signal is typically compared to a library of pre-determined diffraction signals (i.e., simulated diffraction signals) that are associated with known profiles. When a match is made between the measured diffraction signal and one of the simulated diffraction signals, then the profile associated with the matching hypothetical diffraction signal is presumed to represent the profile of the periodic grating.

However, the process of generating a simulated diffraction signal typically involves performing a large number of complex calculations, which can be time consuming and computationally intensive. The amount of time and computational capability and capacity needed to generate simulated diffraction signals can limit the size and resolution (i.e., the number of entries and the increment between entries) of the library of simulated diffraction signals that can be generated. Moreover, the complexity of the measured diffraction signals (i.e., the amount of data) and the potential for the existence of noise can further hinder accurate correlation between measured diffraction signals and simulated diffraction signals. For example, differences in measured diffraction signals can often consist merely of a slight shift or small change in the shape of broad spectral features in the measured diffraction signals.

SUMMARY

In one exemplary embodiment, metrology data from a semiconductor treatment system is transformed using multivariate analysis. In particular, a set of metrology data measured or simulated for one or more substrates treated using the treatment system is obtained. One or more essential variables for the obtained set of metrology data is determined using multivariate analysis. A first metrology data measured or simulated for one or more substrates treated using the treatment system is obtained. The first obtained metrology data is not one of the metrology data in the set of metrology data earlier obtained. The first metrology data is transformed into a second metrology data using the one or more of the determined essential variables.

DESCRIPTION OF DRAWING FIGURES

The present application can be best understood by reference to the following description taken in conjunction with the accompanying drawing figures, in which like parts may be referred to by like numerals.

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

Figure 1:
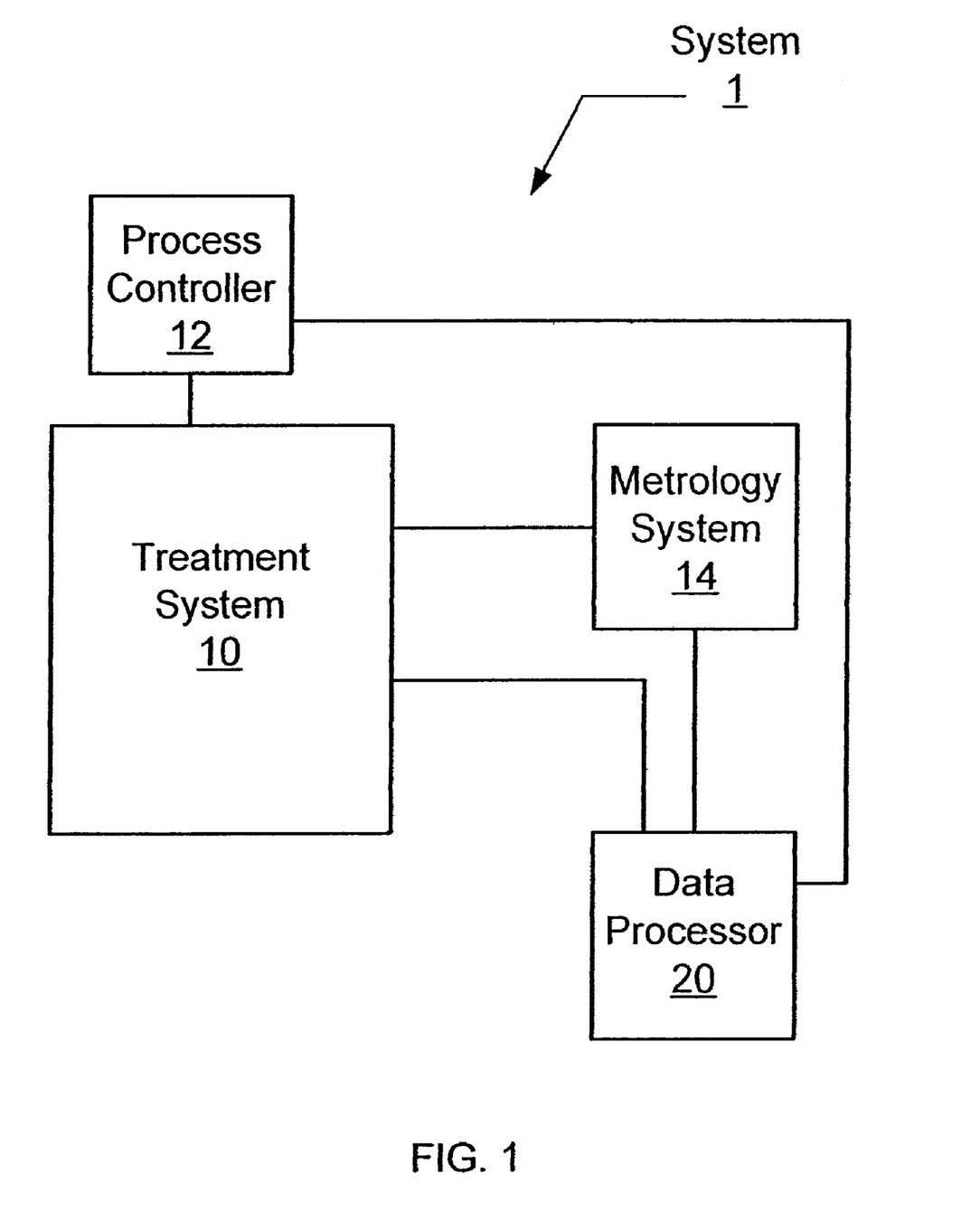
FIG. 1 depicts a schematic view of a processing system according to an embodiment.

Referring now to the drawings, wherein like reference numerals designate identical or corresponding parts throughout the several views, FIG. 1 illustrates a material processing system 1 comprising a semiconductor treatment system 10 configured to treat a substrate, a process controller 12 for performing at least one of monitoring, measuring, adjusting, or controlling, or a combination of two or more thereof, process data for performing a treatment process in treatment system 10. Process data include values of process variables in the treatment process such temperature and time for a treatment process. Material processing system 1 further comprises a metrology system 14 for measuring metrology data from one or more substrates resulting from the treatment process performed in treatment system 10, and a data processor 20. Metrology data includes measurement values of metrology instruments such as scatterometers, CDSEMs, and the like. The process controller 12 is capable of executing the method of performing the treatment process in the treatment system 10. Furthermore, the data processor 20 is coupled to the process controller 12 and the metrology system 14. The data processor 20 is capable of interacting with the process controller 12 and the metrology system 14 and exchanging data therewith, and characterizing the inter-relationships between process data from process controller 12 coupled to treatment system 10 and measured metrology data from metrology system 14 using multivariate analysis.

In the illustrated embodiment, material processing system 1, depicted in FIG. 1, may comprise a lithography system having a track system coupled to a lithographic exposure system, the combination of which is configured to form a film of light-sensitive material, such as photoresist, on a substrate having a pattern, such as an integrated circuit pattern, formed thereon. The patterned film may serve as a patterned mask in a subsequent processing step, such as an etching step. In a process for preparing a lithographic structure, the process data may include, for example, the temperature of the post-application bake (PAB) following the application (or coating) of light-sensitive material to the substrate, the exposure focus during pattern exposure, the exposure dose during pattern exposure, or the temperature of the post-exposure bake (PEB) following pattern exposure. Additionally, the process data may include other parameters such as dispensing rates and spin rates associated with the (light-sensitive material) coating process prior to PAB, or the developing process following PEB.

Alternatively, material processing system 1 may comprise an etching system. The etching system may include a dry etching system or a wet etching system configured to transfer a pattern formed in a mask layer to an underlying layer or layers. For instance, a dry etching system can include a dry plasma etching system configured to facilitate the formation of plasma to assist the creation of chemically reactive constituents and catalyze chemical reactions at the substrate surface. In a process for etching a pattern into an underlying layer, the process data may include, for example, a gas pressure in the treatment system, a flow rate of one or more chemical species (of a process gas) introduced to the treatment system, the power (such as radio frequency (RF) power coupled to the process gas through an electrode in order to facilitate formation of plasma), a time for performing the etching process, or the substrate temperature during processing (which may, in turn, include an electrostatic clamping voltage applied to electrically clamp the substrate to a substrate holder, the temperature of the substrate holder, or a backside pressure of (helium) gas supplied to the backside of the substrate, or any combination thereof, for example).

In another embodiment, material processing system 1 comprises a dielectric coating chamber such as, for example, a spin-on-glass (SOG) or spin-on-dielectric (SOD) system. In another embodiment, material processing system 1 comprises a deposition chamber such as, for example, a chemical vapor deposition (CVD) system, a plasma enhanced CVD (PECVD) system, an atomic layer deposition (ALD) system, a plasma enhanced ALD (PEALD) system, or a physical vapor deposition (PVD) system. In an additional embodiment, material processing system 1 comprises a rapid thermal processing (RTP) chamber such as, for example, a RTP system for thermal annealing. In another embodiment, material processing system 1 comprises a batch diffusion furnace. In yet another embodiment, material processing system 1 can comprise any number of treatment systems found in a semiconductor device manufacturing facility.

Referring still to FIG. 1, metrology system 14 can include an optical metrology system, such as an optical scatterometry system. For instance, the scatterometry system may include an integrated optical digital profilometry scatterometry module configured to measure process performance data resulting from the execution of a treatment process in the treatment system 10. The metrology system 14 may, for example, measure or monitor metrology data resulting from the treatment process. The metrology data can, for example, be utilized to determine process performance data that characterizes the treatment process, such as a process rate, a relative process rate, a feature profile angle, a critical dimension, a feature thickness or depth, a feature shape, etc. For example, in a process for preparing a lithographic structure, process performance data can include a critical dimension (CD), such as a top, middle or bottom CD in a feature (i.e., via, line, etc.), a feature depth, a sidewall angle, a sidewall shape, a spatial distribution of any parameter thereof, a parameter to characterize the uniformity of any spatial distribution thereof, etc. Additionally, for example, in a process for etching a pattern into an underlying layer on a substrate, process performance data can include a critical dimension (CD), such as a top, middle or bottom CD in a feature (i.e., via, line, etc.), a feature depth, a sidewall angle, a sidewall shape, an etch rate, a relative etch rate (e.g., etch selectivity), etc.

The metrology system can be either an in-situ or ex-situ device. For example, the metrology system may include a scatterometer, incorporating beam profile ellipsometry (ellipsometer) and beam profile reflectometry (reflectometer), which is positioned within the transfer chamber (not shown) to analyze substrates transferred into and out of treatment system 10.

Figure 2:
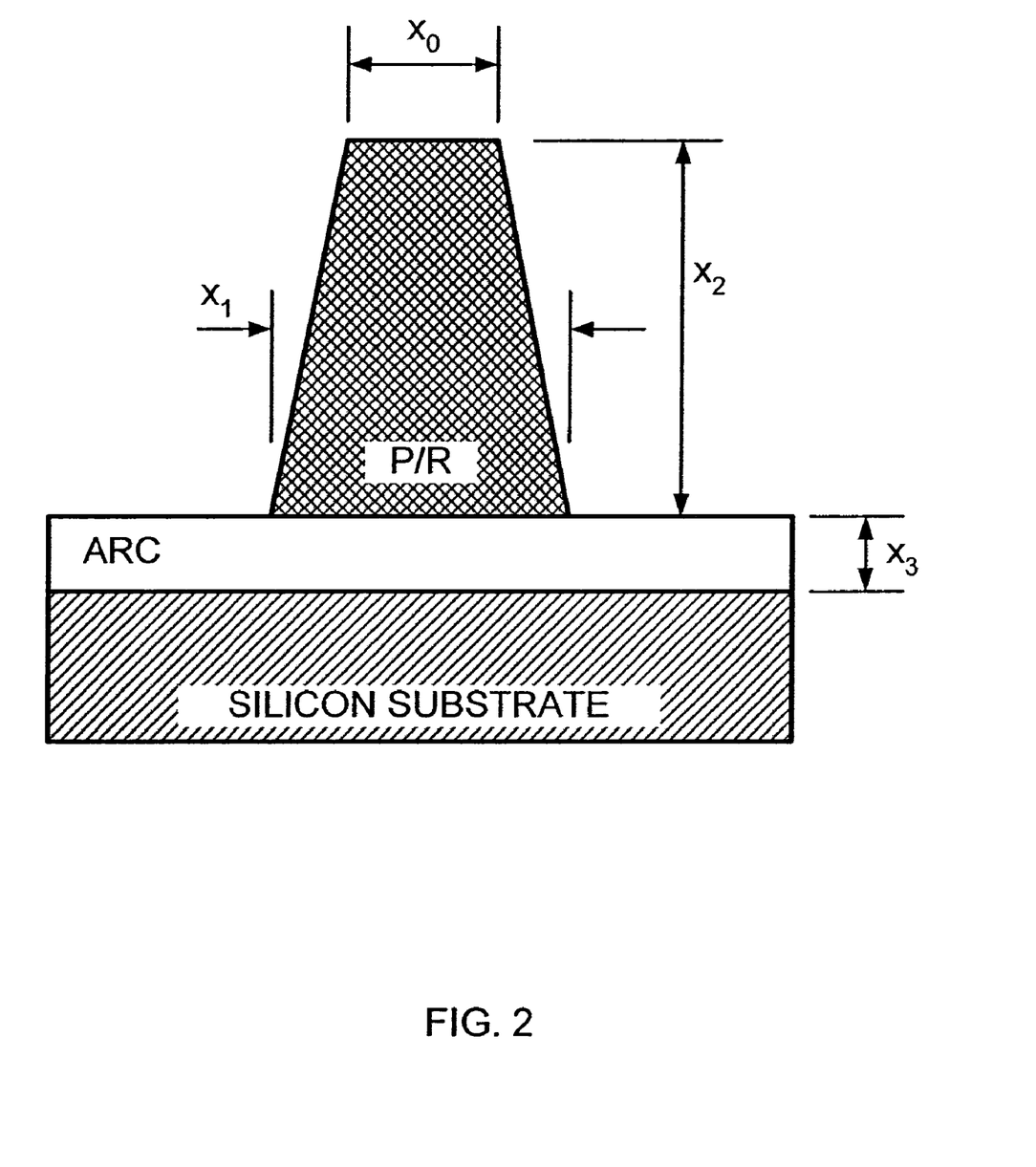
FIG. 2 depicts a schematic view of a structure formed on a substrate according to an embodiment.

When performing optical metrology, such as scatterometry, a structure to be examined on a substrate, such as a semiconductor wafer or flat panel, is illuminated with electromagnetic (EM) radiation, and a diffracted signal received from the structure is utilized to determine the profile of the structure. The structure may include a periodic structure, or a non-periodic structure. Additionally, the structure may include an operating structure on the substrate (e.g., a via or contact hole, or an interconnect line or trench, or a feature formed in a mask layer associated therewith), or the structure may include a periodic grating or non-periodic grating formed proximate to an operating structure formed on a substrate. In this example, the structure to be examined is a periodic grating and can be formed adjacent a transistor formed on the substrate. Alternatively, the periodic grating can be formed in an area of the transistor that does not interfere with the operation of the transistor. The profile of the periodic grating is obtained to determine whether the periodic grating, and by extension the operating structure adjacent the periodic grating, has been fabricated according to specifications. For instance, FIG. 2 illustrates an exemplary structure on a substrate, such as a silicon substrate, having a top critical dimension (CD) $x_0$, a bottom CD $x_1$, and a height $x_2$. Additionally, the structure may reside atop another layer having a thickness $x_3$, such as an anti-reflective coating (ARC) layer. For example, the structure illustrated in FIG. 2 may represent a lithographic structure.

Figure 3:
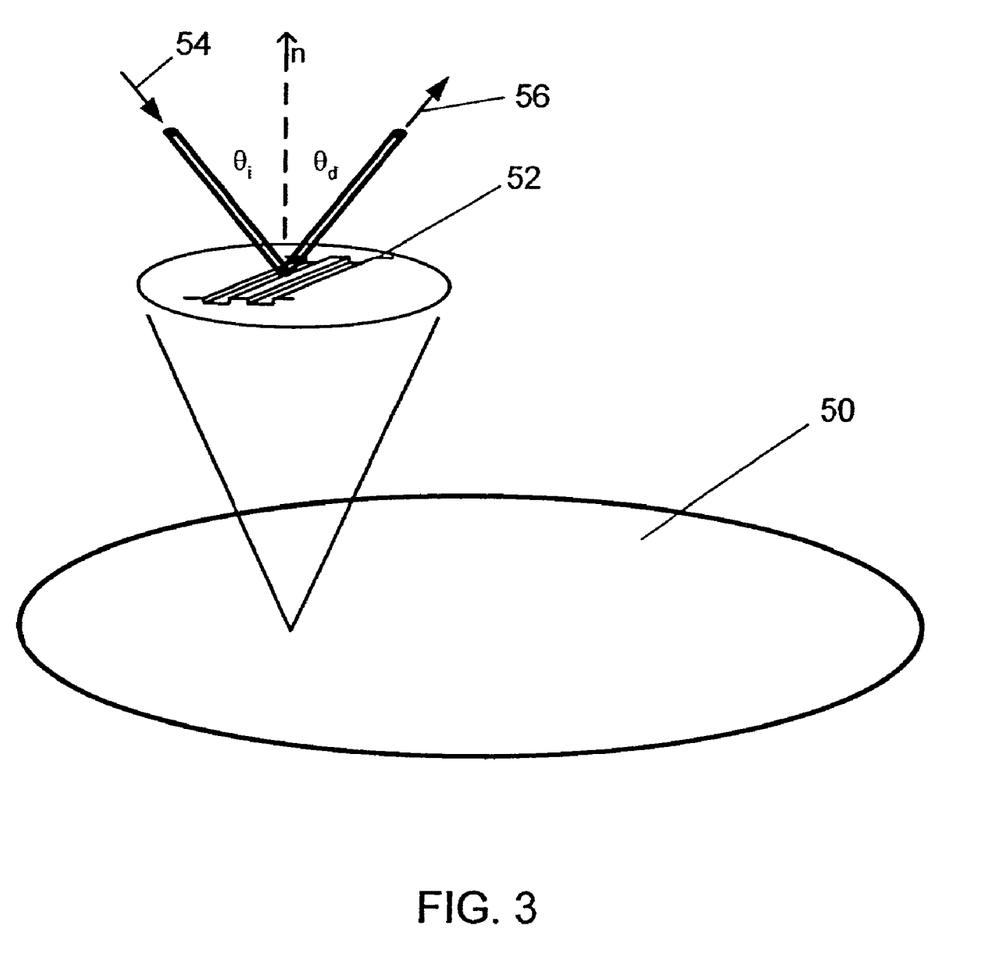
FIG. 3 presents in schematic view a technique for illuminating a structure on a substrate with electromagnetic radiation according to an embodiment.

Referring now to FIG. 3, a periodic grating 52 (or any other type of structure to be examined) on a substrate 50 is illuminated by an incident signal 54 from an EM source, such as an ellipsometer or reflectometer. The incident signal 54 is directed onto the periodic grating 52 at an angle of incidence ($\theta_i$) with respect to the surface normal vector (n) of the periodic grating 52. A diffraction signal 56 leaves the periodic grating 52 at an angle of diffraction ($\theta_d$) with respect to the surface normal vector. In one exemplary embodiment, the angle of incidence is near the Brewster's angle. However, the angle of incidence can vary depending upon the application. For instance, the angle of incidence can range from approximately 0 degrees to approximately 90 degrees.

Figure 4:
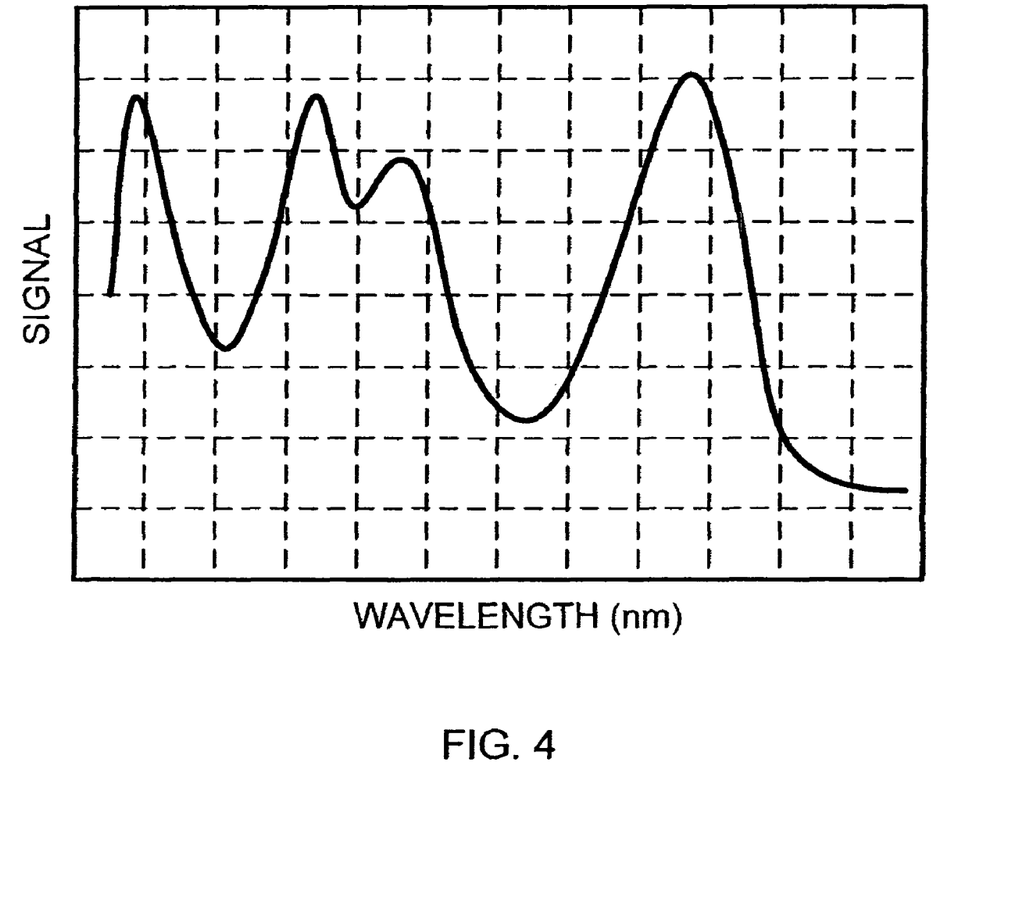
FIG. 4 illustrates an exemplary measured signal obtained from illuminating a structure on a substrate with electromagnetic radiation according to another embodiment.

The diffraction signal is received by a detector and analyzed by a signal processing system. When the EM source is an ellipsometer, the magnitude and the phase of the diffraction signal are received and detected. When the EM source is a reflectometer, the relative intensity of the diffraction signal is received and detected. For instance, FIG. 4 illustrates an exemplary diffraction signal obtained using a scatterometric technique.

The signal processing system compares the diffraction signal received by the detector (i.e., the measured diffraction signal) to simulated diffraction signals stored in a library of simulated diffraction signals Each simulated diffraction signal in the library is associated with a hypothetical profile. When a match is made between the measured diffraction signal and one of the simulated diffraction signals in the library, the hypothetical profile associated with matching simulated diffraction signal is presumed to represent the actual profile of the periodic grating or structure. The matching simulated diffraction signal and/or the hypothetical profile can then be provided to assist in determining whether the periodic grating or structure has been fabricated according to specifications.

In another embodiment, the signal processing system compares the diffraction signal received by the detector to a series of simulated diffraction signals determined in real time. The simulated diffraction signals are determined from an assumed set of profile parameters wherein the next set of profile parameters are altered according to one or more optimization algorithms. For details of the method for generating simulated diffraction signals for real time use or to be used in a library, refer to U.S. Pat. No. 6,943,900, titled "Generation of a library of periodic grating diffraction signals", which is incorporated herein in its entirety.

As described above, the library includes simulated diffraction signals that are associated with hypothetical profiles of the periodic grating or structure formed on the substrate of interest. Typically, the process for preparing the library can include: (1) characterizing the film stack of the periodic grating or structure; (2) obtaining the optical properties of the materials used in forming the periodic grating or structure; (3) obtaining measured diffraction signals from the periodic grating or structure; (4) determining the number of hypothetical parameters (e.g., geometrical parameters, which may be related to process performance parameters such as CD) to use in modeling the profile of the periodic grating or structure; (5) adjusting the range to vary the hypothetical parameters in generating a set of hypothetical profiles; (6) determining the number of layers to use in dividing up a hypothetical profile to generate a simulated diffraction signal for the hypothetical profile; (7) determining the number of harmonic orders to use in generating the set of simulated diffraction signals; (8) determining a resolution to use in generating the set of simulated diffraction signals; (9) and generating the set of simulated diffraction signals based on the adjusted range, parameterization, and/or resolution.

For example, the library can include a range of diffraction signals sufficiently broad to capture the corresponding substrate-to-substrate variations, and batch-to-batch variations, or drift in the set of hypothetical parameters associated with a pre-determined process of record (or nominal process recipe) for performing the specific substrate treatment process. Additionally, for example, the library can include a range of diffraction signals sufficiently broad to capture the corresponding variations in the set of hypothetical parameters associated with a pre-determined process window for performing the specific substrate treatment process.

However, since the relationship between process data (e.g., values of process variables in the treatment process such temperature and time for a treatment process), metrology data (e.g., measurement values of metrology instruments such as scatterometers, CDSEMs, and the like), and process performance data (e.g., data characterizing the treatment process, such as a process rate, a relative process rate, a feature profile angle, a critical dimension, a feature thickness or depth, a feature shape, etc.) are not known a priori, the generation of the library and the determination of a sufficient resolution in generating the library is often very labor-intensive and time consuming, even when there exists some experience regarding these inter-relationships. Moreover, a separate library is required for each application.

Thus, in one embodiment, multivariate analysis, when applied to two or more sets of process data, metrology data, and process performance data, can assist in identifying these inter-relationships. For example, the multivariate analysis can include a linear analysis or a nonlinear analysis. Additionally, for example, the multivariate analysis can include Principal Components Analysis (PCA), Independent Component Analysis, Cross Correlation Analysis, Linear Approximation Analysis, and the like.

In one embodiment, metrology data is collected by obtaining measurements from an actual semiconductor treatment system or from simulations. In particular, in the present example, with continuing reference to FIG. 1, one or more process parameters in the process data can be varied while holding other process parameters constant, metrology data, such as optical spectra received from the substrate, at the beginning or end of each treatment process step (process condition) can be measured or simulated.

The metrology data, e.g., a diffraction signal comprising light intensity as a function of wavelength for each set of process data, can be recorded and stored digitally on data processor 20 as a data matrix $\overline{X}$. For example, each row in the matrix $\overline{X}$ corresponds to a diffraction signal (light intensity versus wavelength) for a given variation in the process data (e.g., a variation in a process parameter). Thus, the different rows of the matrix $\overline{X}$ correspond to different diffraction signal for different variations in the process data. Each column in the matrix $\overline{X}$ corresponds to a specific wavelength in the diffraction signal. Hence, a matrix $\overline{X}$ assembled from metrology data has the dimensions m by n, where, for example, m is the number of measurements and n is the number of wavelengths.

In one exemplary embodiment, statistical data calculations can be performed on the collected metrology data. For example, the data stored in the matrix $\overline{X}$ can be mean-centered and/or normalized, if desired. Centering the data stored in a matrix column involves computing the mean value of the column elements and subtracting it from each element. Moreover, the data residing in a column of the matrix can be normalized by the standard deviation of the data in the column. Furthermore, the centering coefficients and/or normalization coefficients may be updated following each acquisition of new metrology data; for further details, see U.S. patent application Ser. No. 10/660,697, entitled "Method and system of diagnosing a processing system using adaptive multivariate analysis"; the entire content of which is incorporated herein by reference in its entirety. It should be recognized that the step of performing statistical data calculations can be omitted in some applications.

In one exemplary embodiment, multivariate analysis is used to determine the extent to which variations in process data contribute to change in the metrology data (e.g., the spectral signature of each diffraction signal (optical spectrum)). For example, to determine the inter-relationships between variations in process data and the metrology data, the matrix $\overline{X}$ is subject to multivariate analysis.

In one exemplary embodiment, principal components analysis (PCA) is employed to derive a correlation structure within matrix $\overline{X}$ by approximating matrix $\overline{X}$ with a matrix product $(\overline{TP^T})$ of lower dimensions plus an error matrix $\overline{E}$:

$$\overline{X} = \overline{TP^T} + \overline{E}, \quad (1)$$

where $\overline{T}$ is a (m by p) matrix of scores that summarizes the $\overline{X}$-variables and $\overline{P}$ is a (n by p, where $p \leq n$) matrix of loadings showing the influence of the variables.

In general, the loadings matrix $\overline{P}$ can be shown to comprise the eigenvectors of the covariance matrix of $\overline{X}$, where the covariance matrix $\overline{S}$ can be shown to be:

$$\overline{S} = \overline{X}^T \overline{X}. \quad (2)$$

The covariance matrix $\overline{S}$ is a real, symmetric matrix and, therefore, it can be described as:

$$\overline{S} = \overline{U} \overline{\Lambda} \overline{U}^T, \quad (3)$$

where the real, symmetric eigenvector matrix $\overline{U}$ comprises the normalized eigenvectors as columns and $\overline{\Lambda}$ is a diagonal matrix comprising the eigenvalues corresponding to each eigenvector along the diagonal.

Using equations (1) and (3) (for a full matrix of p=n; i.e. no error matrix), the following can be show:

$$\overline{P} = \overline{U} \quad (4)$$

and $$\overline{T}^T \overline{T} = \overline{\Lambda}. \quad (5)$$

A result of the above eigenanalysis is that each eigenvalue represents the variance of the metrology data in the direction of the corresponding eigenvector within n-dimensional space. Hence, the largest eigenvalue corresponds to the greatest variance in the metrology data within the n-dimensional space, while the smallest eigenvalue represents the smallest variance in the metrology data. By definition, all eigenvectors are orthogonal and, therefore, the second largest eigenvalue corresponds to the second greatest variance in the metrology data in the direction of the corresponding eigenvector which is normal to the direction of the first eigenvector.

In one embodiment, one or more essential variables are obtained from performing the multivariate analysis. In particular, one or more of the eigenvalues and eigenvectors from the multivariate analysis is selected as the one or more essential variables. The one or more essential variables can then be used to transform newly acquired metrology data to produce refined metrology data.

In the present example, after performing PCA analysis, the loadings matrix $\overline{P}$ can be utilized to transform new metrology data (e.g., newly acquired (raw) diffraction signal) into refined metrology data (e.g., enhanced diffraction signal) by projecting the new metrology data onto the loadings matrix $\overline{P}$ (or set of principal components) to produce a set of scores (e.g., refined metrology data or enhanced data signal).

In one embodiment, all of the eigenvectors (or principal components) (n) are utilized in the creation of the loadings matrix $\overline{P}$. In an another embodiment, a fraction (<n) of the eigenvectors (or principal components) are utilized in the creation of the loadings matrix $\overline{P}$. For example, the first three to four largest eigenvalues (and corresponding eigenvectors) are chosen to approximate the data and assemble the loadings matrix $\overline{P}$. As a result of the approximation, an error $\overline{E}$ is introduced to the representation in equation (1).

An example of commercially available software which supports PCA modeling is MATLAB, or another is SIMCA-P 8.0; for further details, see the User's Manual (*User Guide to SIMCA-P 8.0: A new standard in multivariate data analysis*, Umetrics AB, Version 8.0, September 1999).

While referring to flow chart 500 in FIG. 9, an application example is provided whereby a treatment process is characterized by defining a process window using one or more calculated principal components (hereinafter referred to as essential variables (EV1, EV2, EV3, ...)). For this example, the treatment process can comprise a process for forming a lithographic structure on a substrate using a treatment system having a track system and an exposure system. As described above, the process data in the preparation of a lithographic structure can include, for example, the temperature of the post-application bake (PAB) following the application (or coating) of light-sensitive material to the substrate, the exposure focus during pattern exposure, the exposure dose during pattern exposure, or the temperature of the post-exposure bake (PEB) following pattern exposure.

While holding two of these process parameters constant (e.g., PAB temperature and PEB temperature), the remaining two process parameters (e.g., exposure focus and dose) are varied over a pre-determined two-dimensional process space. For each process condition, a metrology data (e.g., a diffraction signal such as the one depicted in FIG. 4) is measured and collected as a row in a data matrix ($\overline{X}$) as described above (see 510 in FIG. 9). For instance, as the exposure system steps across a substrate, the exposure focus or dose is varied. One or more substrates may be utilized to assemble the data matrix ($\overline{X}$).

Figure 9:
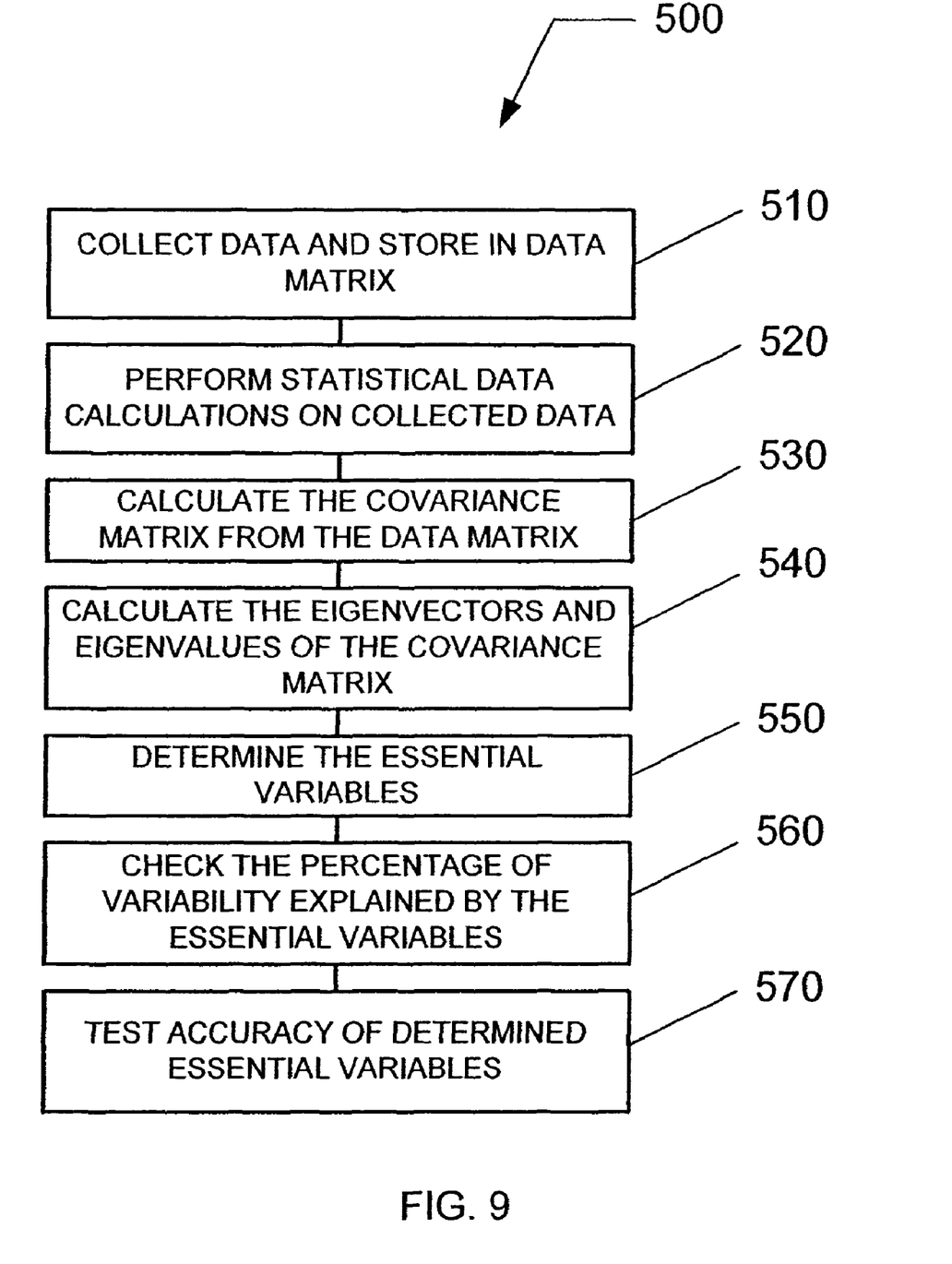
FIG. 9 illustrates a method of determining one or more essential variables according to another embodiment.

Once the data matrix is assembled, the collected data may be optionally subjected to statistical data calculations (see 520 in FIG. 9). The collected data may be mean-centered (e.g., the mean value of the collected data in a column is subtracted from each element in the column). Additionally, the collected data may be normalized (e.g., the collected data in a column may be normalized by the mean value of the collected data in a column or the root mean square (rms) value of the collected data in a column).

Figure 5:
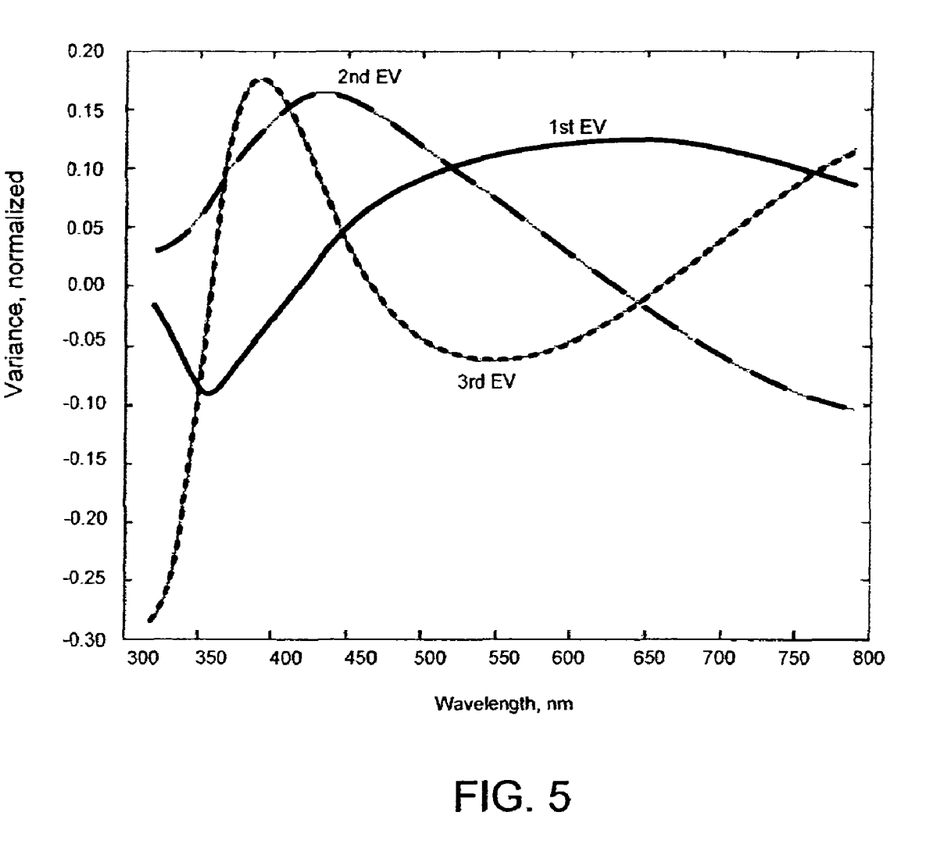
FIG. 5 illustrates exemplary essential variables (EV) for a plurality of measured signals according to an embodiment.

After performing statistical data calculations on the collected metrology data (as shown in 530 of FIG. 9), the covariance matrix is calculated from the data matrix, which may have been subjected to statistical data calculations. Thereafter, as shown in 540 of FIG. 9, the eigenvalues and corresponding eigenvectors are calculated, and, as shown in 550 of FIG. 9, one or more essential variables are identified from the eigenanalysis. For instance, FIG. 5 illustrates an exemplary set of three essential variables (or principal components, or eigenvectors) calculated from a set of metrology data collected for the treatment process configured to prepare a lithographic structure. In the present example, the three essential variables are chosen as the first three eigenvectors following the sorting of the eigenvectors by eigenvalue in order from largest to smallest.

Figure 6:
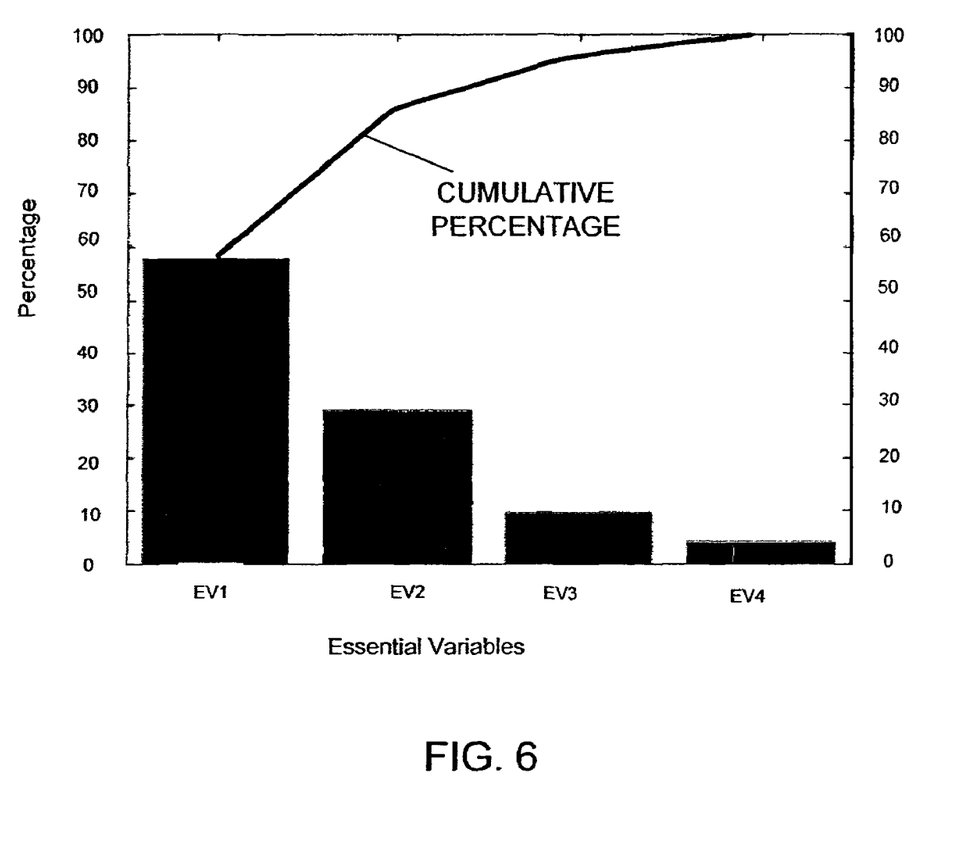
FIG. 6 illustrates exemplary statistical properties for essential variables according to another embodiment.

As shown in 560 of FIG. 9, the percentage of variability explained by each essential variable can be determined. FIG. 6 presents the percentage of variability explained by each of the first four essential variables, as well as the cumulative sum of squares of all of the variables in $\overline{X}$ explained by the extracted principal component(s) for the first four essential variables (or principal components). Thereafter, the accuracy of the determined essential variables may be tested as shown in 570 of FIG. 9.

As described above, multivariate analysis can be applied to two or more sets of process data, metrology data, and process performance data. In the examples described above, multivariate analysis was applied to process data and metrology data. In the following examples, multivariate analysis is applied to metrology data and process performance data.

Figure 7A:
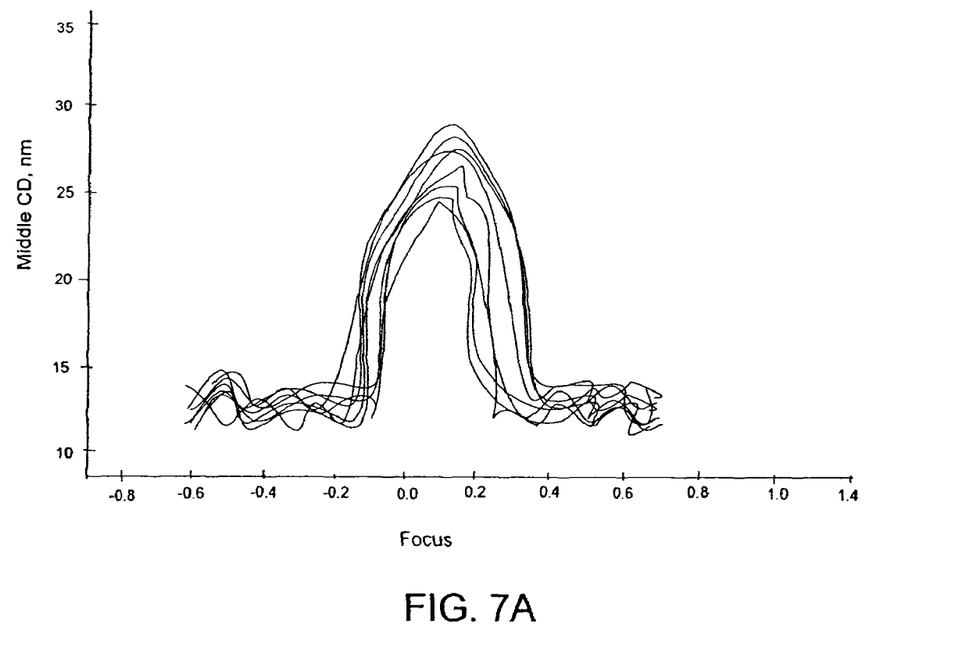
FIG. 7A illustrates exemplary process performance parameter data as a function of two controllable process parameters for a treatment process according to another embodiment.
Figure 8A:
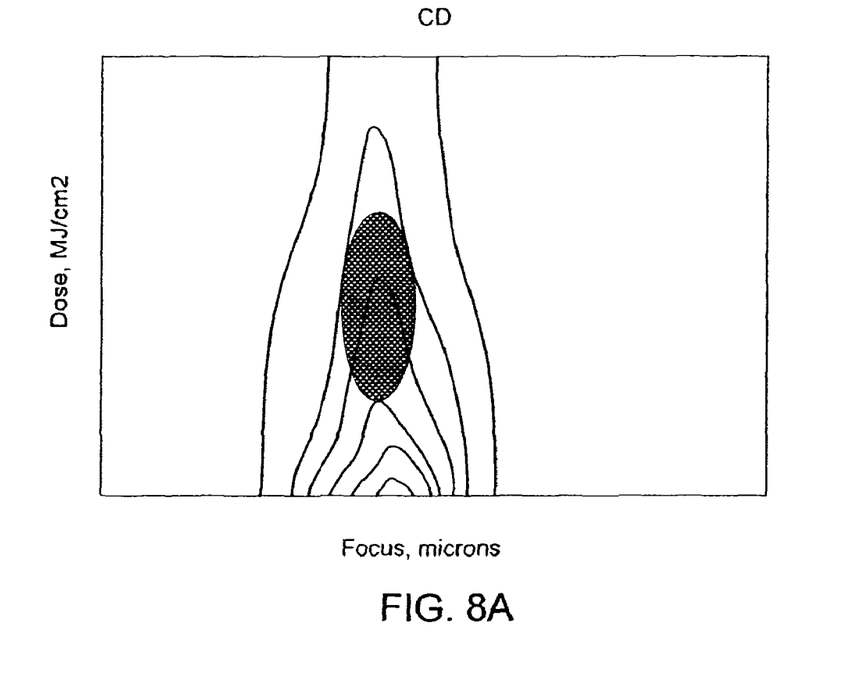
FIG. 8A illustrates an contour plot of exemplary process performance parameter data as a function of two controllable process parameters for a treatment process according to another embodiment.

In one embodiment, referring now to FIGS. 7A and 8A, the metrology data (e.g., diffraction signals) obtained for the matrix of runs performed (whereby exposure focus and dose are varied) can be correlated with process performance data (e.g., feature CD (at the mid-height of the feature)). For example, assume measured diffraction signals are obtained as the metrology data. The measured diffraction signals are matched with simulated diffraction signals stored in a library of diffraction signals (assembled as described above) to determine CD. FIG. 7A presents (mid-height) CD as a function of exposure focus for each value of exposure dose, and FIG. 8A presents a contour plot of CD as a function of both exposure focus and dose. Inspection of FIGS. 7A and 8A indicates that there exists a range of both exposure focus and exposure dose within which the lithographic structure comprises a finite width. For instance, in FIG. 7A, the range of exposure focus is from approximately 0.0 to approximately 0.2. In FIG. 8A, this process range (or acceptable process window) is highlighted by the shaded ellipse.

Figure 7B:
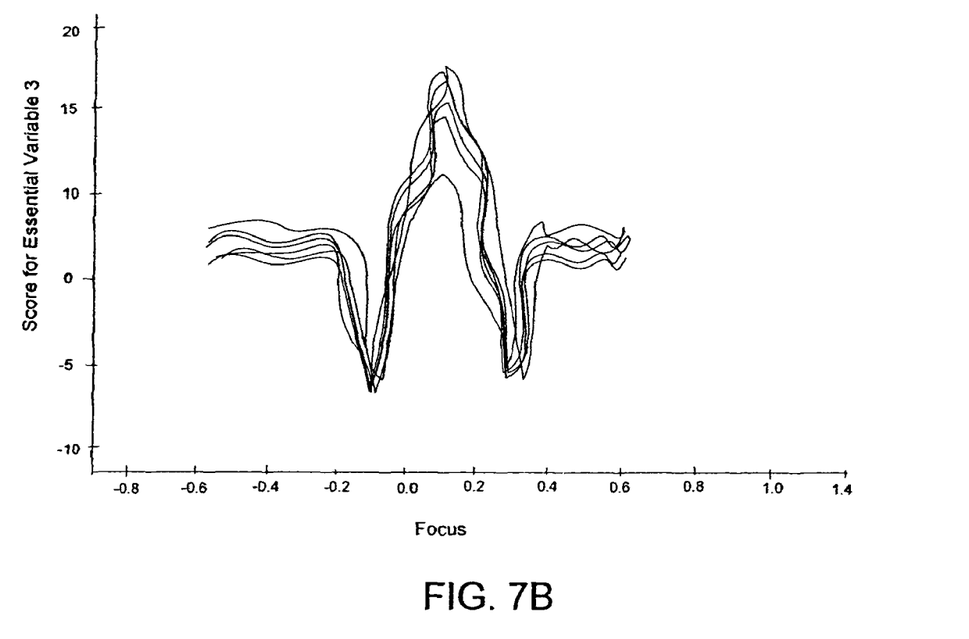
FIG. 7B illustrates exemplary essential variable data as a function of two controllable process parameters for a treatment process according to another embodiment.
Figure 8B:
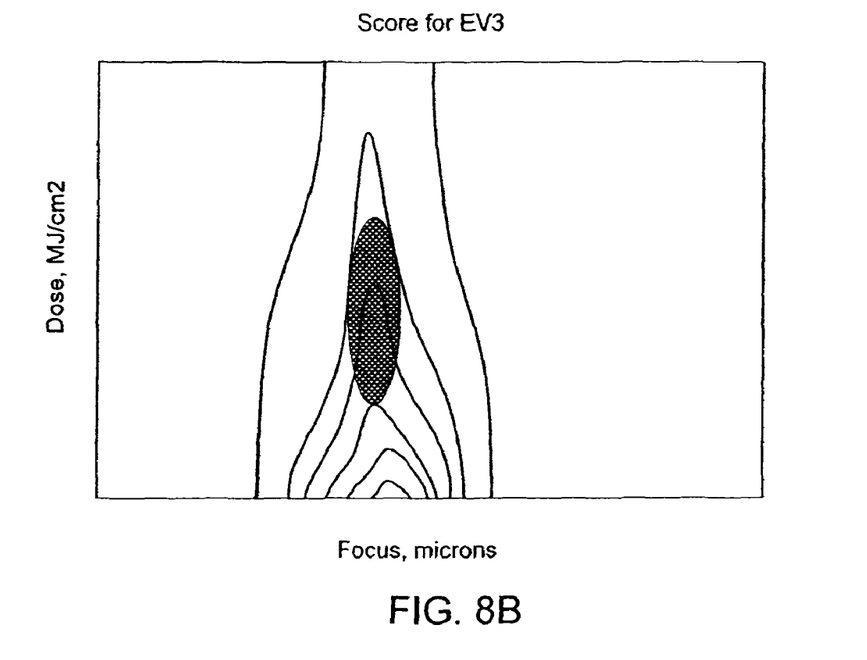
FIG. 8B illustrates an contour plot of exemplary essential variable data as a function of two controllable process parameters for a treatment process according to another embodiment.

Additionally, FIG. 7B presents the score of the third essential variable (i.e., the projection of each diffraction signal (optical spectrum) onto the third essential variable (principal component)) as a function of exposure focus for each value of exposure dose. FIG. 8B presents an contour plot of the score of the third essential variable as a function of both exposure focus and dose. Inspection of FIGS. 7A, 7B, 8A and 8B indicates that an essential variable can be used to characterize a treatment process in a treatment system by, for instance, defining a process window (or space) for the treatment process in the treatment system. For example, if a mid CD of 20 to 30 nm is acceptable, then the range of focus and dose corresponding to the CD of 20-30 nm is considered the process window.

Figure 10:
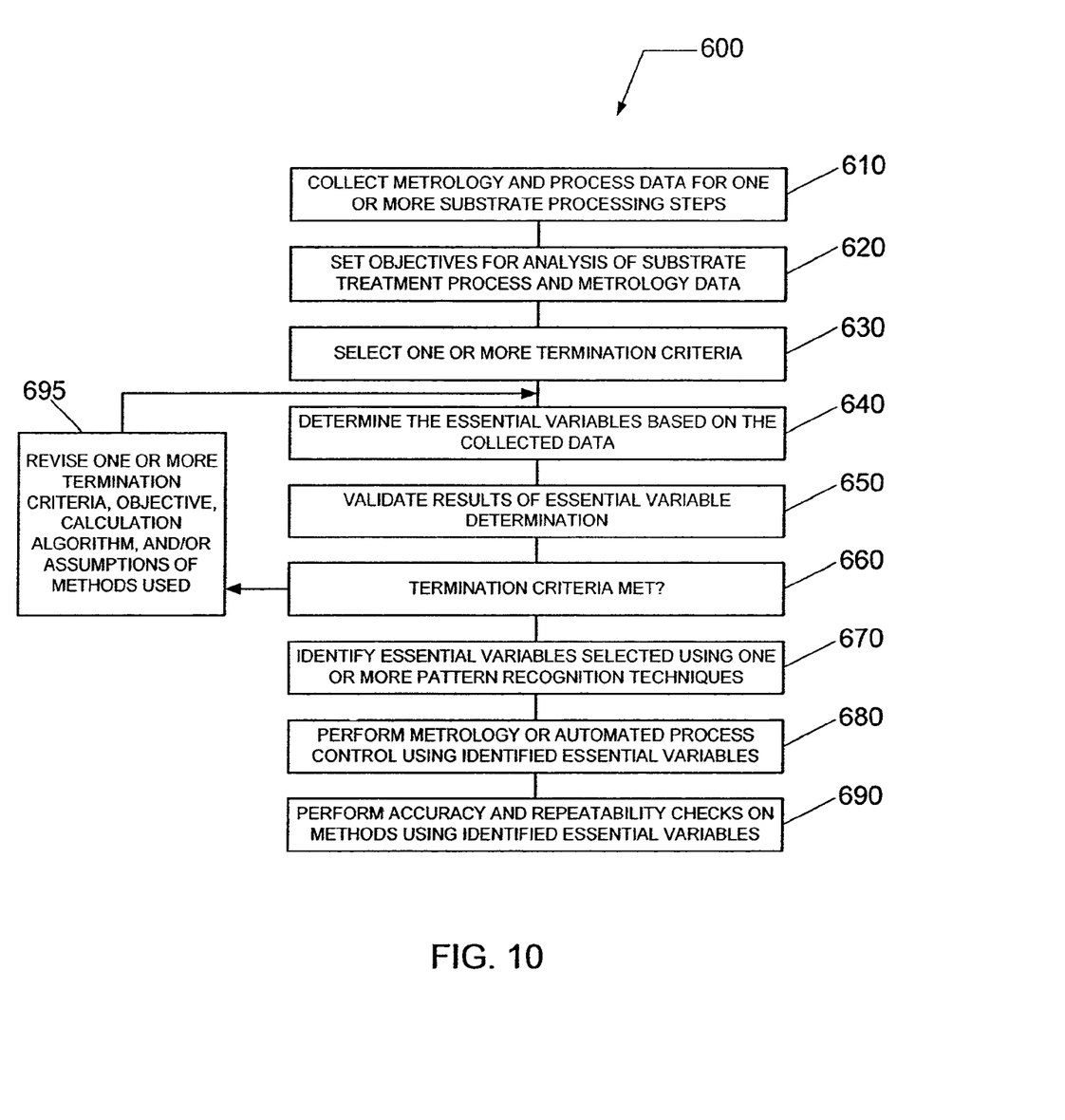
FIG. 10 illustrates a method of operating a treatment system utilizing one or more essential variables according to yet another embodiment.

Referring now to FIG. 10, a method of operating a treatment system to perform a treatment process on one or more substrates is described. The method is represented by a flow chart 600 beginning in 610 with collecting metrology data (e.g., optical spectra, such as diffraction signals), or metrology data and process data for one or more treatment processes or treatment steps.

In 620, objectives are set for the analysis of the treatment process or treatment processes, and the resultant metrology data. For example, the multivariate analysis can be utilized to prepare a model for determining a process window for the treatment process or processes. Alternatively, for example, the multivariate analysis can be utilized to prepare a model for use in a process control algorithm for the treatment process or processes. Alternatively yet, for example, the multivariate analysis can be utilized to prepare a model for use in a process fault detection algorithm for the treatment process or processes.

In 630, one or more termination criteria are set for the analysis of the metrology data. The termination criteria can, for example, include setting a minimum or maximum number of essential variables to be used, or setting one or more statistical parameters for the fraction of variance in the metrology data to be explained by the essential variables.

In 640, multivariate analysis is performed on a set of the collected metrology data. For example, the multivariate analysis can include principal components analysis (PCA). Additionally, for example, the collected metrology data can comprise a plurality of diffraction signals (or optical spectra acquired from illuminating a structure on the one or more substrates) from an optical metrology system.

In 650, the determination of the essential variables can be validated. For example, the essential variables may be inspected, as in FIG. 5, and the ability of the essential variables to explain the variation in the metrology data can be verified, as in FIG. 6.

In 660, the results of the multivariate analysis are checked to ensure that the pre-selected termination criteria are met. If not, in 695, one or more of the termination criteria, the analysis objectives, the multivariate analysis (calculation) algorithm, or any of the assumptions employed in the analysis can be adjusted.

In 670, one or more of the essential variables is selected for use with future metrology data. For example, one or more essential variables can be utilized to transform old metrology data, new metrology data, or test metrology data, or a combination thereof into refined metrology data, such as a score resulting from the projection of a diffraction signal onto an essential variable.

This refined metrology data, i.e., a score, can be compared with process performance data, such as a critical dimension, that is recovered from the conventional technique of matching the diffraction signal with a library of known signals and profiles. Alternatively, this refined metrology data can be compared with process performance data, such as critical dimension, that is recovered from SEM measurements. In doing so, as depicted in FIGS. 7A, 7B, 8A and 8B, one or more essential variables can be selected which produce refined metrology data that best correlates with the process performance data, i.e., the critical dimension, etc.

The inspection of the data in FIGS. 7A, 7B, 8A and 8B may be performed by an operator skilled in the art of such analysis, or it may be performed using one or more pattern recognition techniques. For example, the shape of the curve in FIG. 7A (focus v. mid CD) has approximately the same pattern as the curve in FIG. 7B (focus v. essential variable 3). Thus, essential variable 3 is assumed to correspond to mid CD, and focus can be correlated to mid CD. Based on this correlation, an input focus value can be used in the treatment process to determine the mid CD.

During step 670, a calibration between the refined metrology data and the process performance data can be achieved. The calibration can then be used to predict process performance data, such as a critical dimension.

In yet another embodiment, the calibration (or relationship) between refined metrology data, such as PCA scores, and process performance data can be determined using partial least-squares (PLS) analysis, classical least squares (CLS), inverse least squares (ILS), or the like, or neural networks.

For example, in PLS analysis, a plurality of observations (metrology data) of diffraction signals (or optical spectra) can be acquired for a range of process performance data, such as critical dimension (CD), that may be representative of the typical variations for the specific treatment process. Each metrology data (such as a diffraction signal) can be transformed into refined metrology data by determining the projection of each diffraction signal onto a set of pre-determined essential variables. Then, each array of refined metrology data can be stored as a row of a new data matrix $\overline{X}$, and the corresponding process performance data (e.g., CD, etc.) can be stored as a row in a second new data matrix $\overline{Y}$.

Once the data is assembled into their respective matrices, the following relationship can be solved using PLS analysis:

$$\overline{X}\overline{B}' = \overline{Y}, \quad (7)$$

where $\overline{X}'$ represents the m by n matrix described above containing the refined metrology data, $\overline{B}'$ represents an n by p (p<n) loading (or correlation) matrix, and $\overline{Y}'$ represents the m by p matrix containing the process performance data.

Once the data matrix $\overline{X}'$ and the endpoint signal matrix $\overline{Y}'$ are assembled, a relationship designed to best approximate the $\overline{X}'$ and $\overline{Y}'$ spaces and to maximize the correlation between $\overline{X}'$ and $\overline{Y}'$ is established using PLS analysis.

In the PLS analysis, the matrices $\overline{X}'$ and $\overline{Y}'$ are decomposed as follows:

$$\overline{X}' = \overline{T}\overline{P}^T + \overline{E}, \quad (7a)$$

$$\overline{Y}' = \overline{U}\overline{C}^T + \overline{F}, \quad (7b)$$

$$\overline{U} = \overline{T} + \overline{H}, \quad (7c)$$

where $\overline{T}$ is a matrix of scores that summarizes the $\overline{X}'$ variables, $\overline{P}$ is a matrix of loadings for matrix $\overline{X}'$, $\overline{U}$ is a matrix of scores that summarizes the $\overline{Y}'$ variables, $\overline{C}$ is a matrix of weights expressing the correlation between $\overline{Y}'$ and $\overline{T}(\overline{X}')$, and $\overline{E}$, $\overline{F}$ and $\overline{H}$ are matrices of residuals. Furthermore, in the PLS analysis, there are additional loadings $\overline{W}$ called weights that correlate $\overline{U}$ and $\overline{X}'$, and are used to calculate $\overline{T}$.

In summary, the PLS analysis geometrically corresponds to fitting a line, plane or hyper plane to both the $\overline{X}'$ and $\overline{Y}'$ data represented as points in a multidimensional space, with the objective of well approximating the original data tables $\overline{X}'$ and $\overline{Y}'$, and maximizing the covariance between the observation positions on the hyper planes.

An example of commercially available software which supports PLS analysis is MATLAB, or another is SIMCA-P 8.0; for further details, see the User's Manual (*User Guide to SIMCA-P 8.0: A new standard in multivariate data analysis*, Umetrics AB, Version 8.0, September 1999).

In 680, once a PCA model is prepared, i.e., one or more essential variables are determined to characterize the treatment process or processes, the one or more essential variables are utilized to perform one or more of the following: characterization of the treatment process or processes; monitoring of the treatment process or processes; adjusting of the treatment process or processes; automated control of the treatment process or processes; or fault detection for the treatment process or processes. For example, during characterization of a treatment process or processes, the one or more selected essential variables may be used to define a process window, as illustrated in FIGS. 7A, 7B, 8A and 8B.

Alternatively, for example, the one or more selected essential variables may be utilized to predict the change in process performance data from one substrate to the next, or one batch of substrates to the next, using metrology data from the current treatment process and a preceding treatment process. The change in either metrology data or process performance data can be correlated with an adjustment to process data (using the multivariate analysis from above). The adjustment to the process data, with or without a filter, may be performed in order to correct the observed variation or drift in metrology data or process performance data.

Yet alternatively, for example, the one or more selected essential variables may be utilized to predict a fault in a treatment process or processes, or it may be utilized to predict a drifting treatment process or processes. The one or more selected essential variables may be used to transform metrology data into refined metrology data. Statistics, such as the variance or root-mean-square variation, of the set of refined metrology data may be used to determine the occurrence of a fault or drifting treatment process. For instance, when the refined metrology data, or a change in the refined metrology data, or a statistical parameter of the refined metrology data exceeds a pre-determined threshold, a fault or drifting process is deemed to have occurred.

In 690, the accuracy of the essential variables can be checked and re-checked. The one or more essential variables can be used to transform the metrology data into refined metrology data, and this refined metrology data may or may not be correlated with process performance data as, for example, described above. The refined metrology data can be compared with old (verified) metrology data, or the predicted process performance data may be compared with process performance data acquired by conventional techniques, such as library matching, or real-time simulation, or SEM data.

Figure 11:
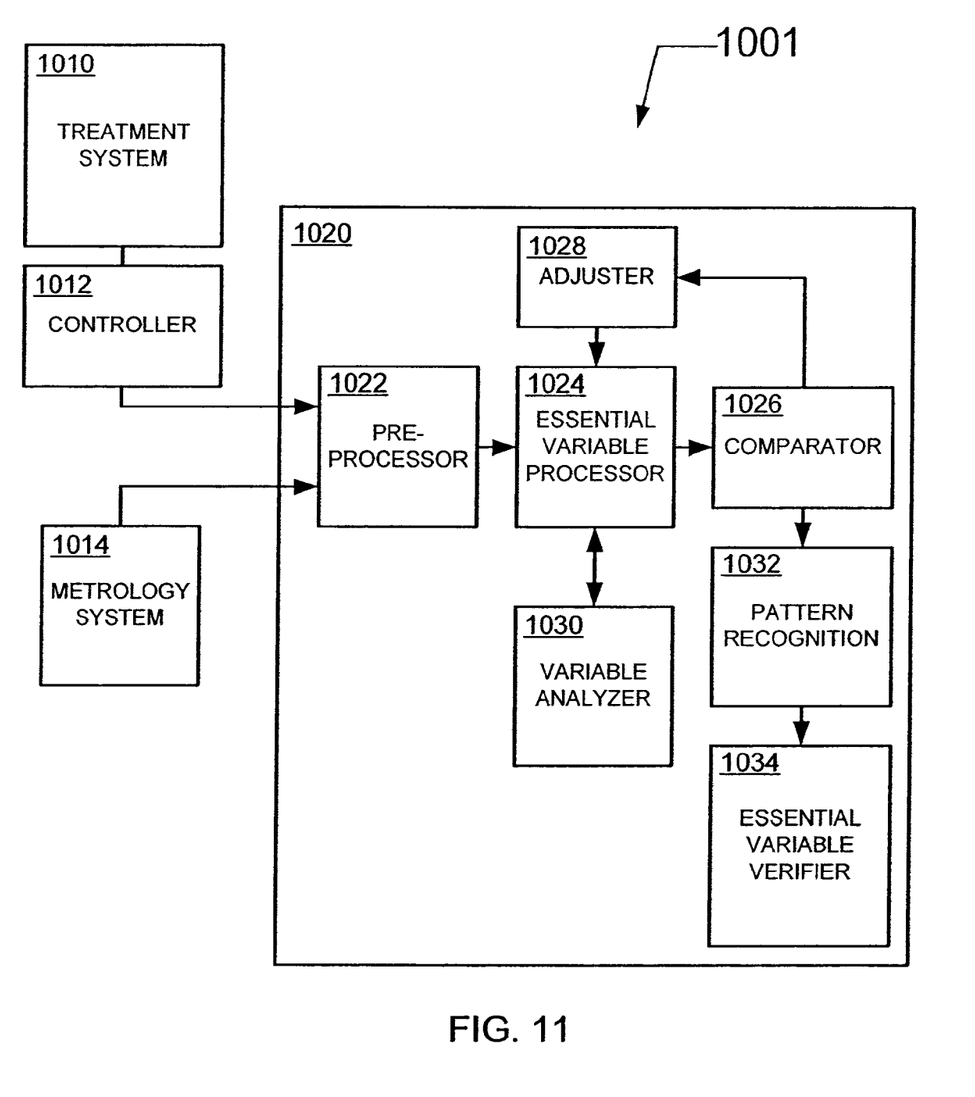
FIG. 11 depicts a schematic view of a processing system according to yet another embodiment.

Referring now to FIG. 11, a material processing system 1001 comprising a data processing system 1020 is depicted for operating a treatment system 1010 via controller 1012 and a metrology system 1014 according to, for example, the method described above. The controller 1012 is configured to perform at least one of monitoring, measuring, adjusting, or controlling, or a combination of two or more thereof, process data for performing a treatment process in treatment system 1010. The controller 1012 is capable of executing the method of performing the treatment process in the treatment system 1010. The metrology system 1014 is configured to measure metrology data from one or more substrates resulting from the treatment process performed in treatment system 1010.

Furthermore, the data processing system 1020 is coupled to the controller 1012 and the metrology system 1014. The data processing system 1020 is capable of interacting with the controller 1012 and the metrology system 1014 and exchanging data therewith, and characterizing the inter-relationships between process data from controller 1012 coupled to treatment system 1010 and measured metrology data from metrology system 1014 using multivariate analysis.

Referring still to FIG. 11, data processing system 1020 comprises a pre-processor configured to pre-process process data and metrology data for data processing system 1020. For example, the pre-processor 1022 may center and normalize metrology data prior to determination of essential variables. Additionally, data processing system 1020 comprises an essential variable processor 1024 configured to exchange data with pre-processor 1022 and determine essential variables using multivariate analysis. Furthermore, the essential variable processor 1024 may be configured to transform metrology data into refined metrology data for use with a treatment process or processes. A variable analyzer 1030, coupled to the essential variable processor 1024, may be utilized to validate the calculated essential variables. Furthermore, a comparator 1026, coupled to the essential variable processor 1024, may be used to determine whether the pre-defined termination criteria have been met, and adjuster 1028 may be configured to adjust one or more of the termination criteria, the analysis objective, the multivariate analysis (calculation) algorithm, or any of the assumption imposed during the analysis.

Additionally, pattern recognition software 1032, such as PLS analysis or other analysis techniques, may be utilized to determine a correlation between refined metrology data and process performance data, and an essential variable verifier 1034 may be used to check the accuracy, or the repeatability of the utilization of the one or more essential variables to characterize, monitor, adjust, or control the treatment process in the treatment system.

Referring still to FIG. 11, the data processing system 1020 can comprise a microprocessor, a memory, and a digital I/O port capable of generating control voltages sufficient to communicate and activate inputs of the controller 1012 and the metrology system 1014, as well as monitor outputs from the controller 1012 and metrology system 1014. Moreover, the data processing system 1020 is coupled to and exchanges information with treatment system 1010. One example of data processing system 1020 is a DELL PRECISION WORKSTATION 610™, available from Dell Corporation, Dallas, Tex. The data processing system 1020 may also be implemented as a general-purpose computer, digital signal process, etc.

However, the data processing system 1020 may be implemented as a general purpose computer system that performs a portion or all of the microprocessor based processing steps of the invention in response to a processor executing one or more sequences of one or more instructions contained in a memory. Such instructions may be read into the controller memory from another computer readable medium, such as a hard disk or a removable media drive. One or more processors in a multi-processing arrangement may also be employed as the controller microprocessor to execute the sequences of instructions contained in main memory. In alternative embodiments, hard-wired circuitry may be used in place of or in combination with software instructions. Thus, embodiments are not limited to any specific combination of hardware circuitry and software.

The data processing system 1020 includes at least one computer readable medium or memory, such as the controller memory, for holding instructions programmed according to the teachings of the invention and for containing data structures, tables, records, or other data that may be necessary to implement the present invention. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Software for controlling the data processing system 1020, for driving a device or devices, and/or for enabling the controller to interact with a human user can be stored on any one or on a combination of computer readable media. Such software may include, but is not limited to, device drivers, operating systems, development tools, and applications software. Such computer readable media further includes the computer program product for performing all or a portion (if processing is distributed) of the processing described above.

The computer code devices may be any interpretable or executable code mechanism, including but not limited to scripts, interpretable programs, dynamic link libraries (DLLs), Java classes, and complete executable programs. Moreover, parts of the processing may be distributed for better performance, reliability, and/or cost.

The term "computer readable medium" as used herein refers to any medium that participates in providing instructions to the processor of the data processing system 1020 for execution. A computer readable medium may take many forms, including but not limited to, non-volatile media, volatile media, and transmission media. Non-volatile media includes, for example, optical, magnetic disks, and magneto-optical disks, such as the hard disk or the removable media drive. Volatile media includes dynamic memory, such as the main memory. Moreover, various forms of computer readable media may be involved in carrying out one or more sequences of one or more instructions to processor of controller for execution. For example, the instructions may initially be carried on a magnetic disk of a remote computer. The remote computer can load the instructions remotely into a dynamic memory and send the instructions over a network to the data processing system 1020.

Data processing system 1020 may be locally located relative to the treatment system 1010, or it may be remotely located relative to the treatment system 1010 via an internet or intranet. Thus, data processing system 1020 can exchange data with the treatment system 1010 using at least one of a direct connection, an intranet, or the internet. Data processing system 1020 may be coupled to an intranet at a customer site (i.e., a device maker, etc.), or coupled to an intranet at a vendor site (i.e., an equipment manufacturer). Furthermore, another computer (i.e., controller, server, etc.) can access data processing system 1020 to exchange data via at least one of a direct connection, an intranet, or the internet.

Although exemplary embodiments have been described, various modifications can be made without departing from the spirit and/or scope of the present invention. Therefore, the present invention should not be construed as being limited to the specific forms shown in the drawings and described above.

We claim:

1. A method for operating a treatment system, comprising:
collecting metrology data from one or more substrates treated by a treatment process in said treatment system;
setting objectives for an analysis of said treatment process and said metrology data;
selecting one or more termination criteria for performing said analysis;
determining one or more essential variables from said metrology data using multivariate analysis;
validating said one or more essential variables by computing one or more statistics associated with the explanation of said metrology data by said one or more essential variables;
determining whether said one or more termination criteria is achieved;
adjusting said one or more termination criteria, or said analysis objectives, or said multivariate analysis, or any combination of two or more thereof if said one or more termination criteria are not achieved;
identifying at least one of said one or more essential variables using one or more pattern recognition techniques;
utilizing said at least one of said one or more essential variables to characterize said treatment process, or adjust said treatment process, or monitor said treatment process, or control said treatment process, or detect a fault in said treatment process, or a combination of two or more thereof; and performing an accuracy check, or repeatability check, or both on said utilization of said at least one of said one or more essential variables, wherein said collecting said metrology data comprises collecting optical metrology data, and wherein said collecting said optical metrology data comprises collecting an optical signal resulting from illuminating one or more structures on said one or more substrates with an incident optical signal.

2. The method of claim 1, wherein said one or more structures includes a periodic structure or a non-periodic structure on said one or more substrates.

3. The method of claim 1, wherein said one or more structures includes one or more periodic structures formed proximate to or on scribe lines on said one or more substrates, said one or more structures includes an operating structure on said one or more substrates.

4. The method of claim 1, wherein said collecting said metrology data comprises collecting a plurality of diffraction signals from optical illumination of said one or more substrates.

5. The method of claim 1, wherein said using multivariate analysis comprises using a linear analysis or a nonlinear analysis.

6. The method of claim 1, wherein said determining one or more essential variables comprises calculating one or more principal components from a set of said metrology data using principal components analysis (PCA).

7. The method of claim 1, wherein said identifying at least one of said one or more essential variables using one or more pattern recognition techniques comprises determining a relationship between said refined metrology data and process performance data related to the profile of said one or more structures on said one or more substrates.

8. A treatment system for preparing a lithographic structure on a substrate, comprising:

a track system configured to coat one or more substrates with a film of light-sensitive material, and develop a pattern in said film of light-sensitive material following exposure of said film of light-sensitive material to radiation;

an exposure system coupled to said track system, and configured to expose said film of light-sensitive material to radiation;

a metrology system to measure a set of metrology data from for said one or more substrates treated in said track system and said exposure system for variations in process data for said track system and said exposure system, wherein said process data comprises an exposure focus in said exposure system, an exposure dose in said exposure system, a temperature of a post-application bake of said layer of light-sensitive material preceding said exposure, or a temperature of a post-exposure bake of said layer of light-sensitive material following said exposure, or any combination of two or more thereof;

a data processing system configured to:
 obtain said set of metrology data;
 determine one or more essential variables for said obtained set of metrology data using multivariate analysis;
 obtain new metrology data measured using said metrology system; and
 transform said new metrology data into refined metrology data using said one or more essential variables,
wherein said metrology data comprises optical metrology data, and
wherein said optical metrology data comprises an optical signal resulting from illuminating one or more structures on said one or more substrates with an incident optical signal.

9. The treatment system of claim 8, wherein said data processing system is further configured to:

correlating at least one of said one or more essential variables with a critical dimension of said lithographic structure formed in said layer of light-sensitive material following treatment in said track system and said exposure system; and selecting said at least one of said one or more essential variables that correlates with said critical dimension to transform said new metrology data.

10. The treatment system of claim 8, further comprising:

a controller coupled to said track system, or said exposure system, or both, and configured to control said track system, or said exposure system, or both using refined metrology data.

11. The treatment system of claim 8, wherein said metrology system comprises an optical metrology system, and wherein said multivariate analysis comprises principal components analysis (PCA).

* * * * *